US012642760B2

(12) United States Patent (10) Patent No.: US 12,642,760 B2

Lathuilière et al. (45) Date of Patent: Jun. 2, 2026

(54) IMPLANTABLE CAPSULE

(71) Applicants: RELEASE THERAPEUTICS SA,
Geneva (CH); **LES HOPITAUX
UNIVERSITAIRES DE GENÈVE**,
Geneva (CH); **UNIVERSITE DE
GENEVE**, Geneva (CH)

(72) Inventors: Aurélien Lathuilière, Geneva (CH);
Julien Grogg, Lausanne (CH); **Nicolas
Mach**, Collonge-Bellerive (CH)

(73) Assignees: RELEASE THERAPEUTICS SA,
Geneva (CH); **LES HOPITAUX
UNIVERSITAIRES DE GENÈVE**,
Geneva (CH); **UNIVERSITE DE
GENEVE GENEVE**, Geneva (CH)

( * ) Notice: Subject to any disclaimer, the term of this
patent is extended or adjusted under 35
U.S.C. 154(b) by 1067 days.

(21) Appl. No.: 17/635,011

(22) PCT Filed: Aug. 12, 2020

(86) PCT No.: PCT/EP2020/072673
§ 371 (c)(1),
(2) Date: Feb. 14, 2022

(87) PCT Pub. No.: WO2021/028502
PCT Pub. Date: Feb. 18, 2021

(65) Prior Publication Data
US 2022/0287959 A1 Sep. 15, 2022

(30) Foreign Application Priority Data

Aug. 14, 2019 (EP) ..................................... 19191868

(51) Int. Cl.
*A61K 9/00* (2006.01)
*A61K 35/34* (2015.01)
(Continued)

(52) U.S. Cl.
CPC ............ *A61K 9/0024* (2013.01); *A61K 35/34*
(2013.01); *A61K 38/193* (2013.01); *A61L
27/26* (2013.01);
(Continued)

(58) Field of Classification Search
CPC ........ A61K 9/0024; A61K 9/48; A61K 35/34;
A61L 2300/62; A61L 2300/64; A61F
2/022
See application file for complete search history.

(56) References Cited

U.S. PATENT DOCUMENTS

| | | | |
|---|---|---|---|
| 6,303,136 B1 | 10/2001 | Li et al. | |
| 8,892,217 B2 | 11/2014 | Camps et al. | |
| 2022/0265727 A1 | 8/2022 | Lathuilière et al. | |

FOREIGN PATENT DOCUMENTS

| | | |
|---|---|---|
| CN | 104640579 | 5/2015 |
| JP | 2018-515582 | 6/2018 |

(Continued)

OTHER PUBLICATIONS

Grogg, J. et al. "Engineering a versatile and retrievable cell micro-
encapsulation device for the delivery of therapeutic proteins" *iScience*,
Aug. 18, 2023, pp. 1-22, vol. 26, No. 107372.

(Continued)

*Primary Examiner* — Carlos A Azpuru
(74) *Attorney, Agent, or Firm* — SALIWANCHIK,
LLOYD & EISENSCHENK

(57) ABSTRACT

Implantable capsule comprising a cell receiving portion (2)
comprising a porous membrane (5) surrounding a cell
receiving chamber (13) for receiving immortalized cells in a
liquid media therein for the secretion of therapeutic agents.
The capsule further comprises a cell support matrix (7)

(Continued)

inserted within the cell receiving chamber (13) configured for the arrangement of the immortalized cells within the cell receiving chamber.

17 Claims, 2 Drawing Sheets

(51) Int. Cl.

| | | |
|---|---|---|
| *A61K 38/19* | (2006.01) | |
| *A61L 27/26* | (2006.01) | |
| *A61L 27/38* | (2006.01) | |

(52) U.S. Cl.
CPC ....... *A61L 27/3826* (2013.01); *A61L 2300/62* (2013.01)

(56) References Cited

FOREIGN PATENT DOCUMENTS

| | | |
|---|---|---|
| RU | 2 201 765 | 4/2003 |
| WO | WO 97/15195 | 5/1997 |
| WO | WO 01/43696 | 6/2001 |
| WO | WO 2012/075184 | 6/2012 |
| WO | WO 2013/181424 | 12/2013 |
| WO | WO 2014/173441 | 10/2014 |
| WO | WO 2016/191645 | 12/2016 |
| WO | 2017/064571 A1 * | 4/2017 |
| WO | WO 2017/064571 | 4/2017 |
| WO | WO 2021/028500 | 2/2021 |

OTHER PUBLICATIONS

Farina, M. et al. "Cell encapsulation: Overcoming barriers in cell transplantation in diabetes and beyond" *Advanced Drug Delivery Reviews,* available online Apr. 30, 2018, pp. 92-115, vol. 139.

Lathuilière, A. et al. "A high-capacity cell macroencapsulation system supporting the long-term survival of genetically engineered allogeneic cells" *Biomaterials,* available online Oct. 5, 2013, pp. 779-791, vol. 35.

Lathuilière, A. et al. "Encapsulated Cellular Implants for Recombinant Protein Delivery and Therapeutic Modulation of the Immune System" *Int. J. Mol. Sci.,* 2015, pp. 10578-10600, vol. 16.

Mach, N. et al. "Cell-based immunotherapy combining encapsulation cell technology and irradiated autologous tumor cells: A novel technology platform that is both safe and feasible. Results from first in man trial" *Annals of Oncology,* 2015, p. 1, vol. 26, Supplement 8.

Salmon, P. "Generation of Human Cell Lines Using Lentiviral-Mediated Genetic Engineering" *Chapter 25 in Epithelial Cell Culture Protocols: Second Edition, Methods in Molecular Biology,* Scott H. Randell and M. Leslie Fulcher (eds.), 2012, pp. 417-448, vol. 945.

Schwenter, F. et al. "Cell encapsulation technology as a novel strategy for human anti-tumor immunotherapy" *Cancer Gene Therapy,* published online May 13, 2011, pp. 553-562, vol. 18.

Townsend-Nicholson, A. et al. "Cell Electrospinning: a Unique Biotechnique for Encapsulating Living Organisms for Generating Active Biological Microthreads/Scaffolds" *Biomacromolecules,* 2006, pp. 3364-3369, vol. 7, No. 12.

Written Opinion in International Application No. PCT/EP2020/072673, Oct. 15, 2020, pp. 1-14.

* cited by examiner

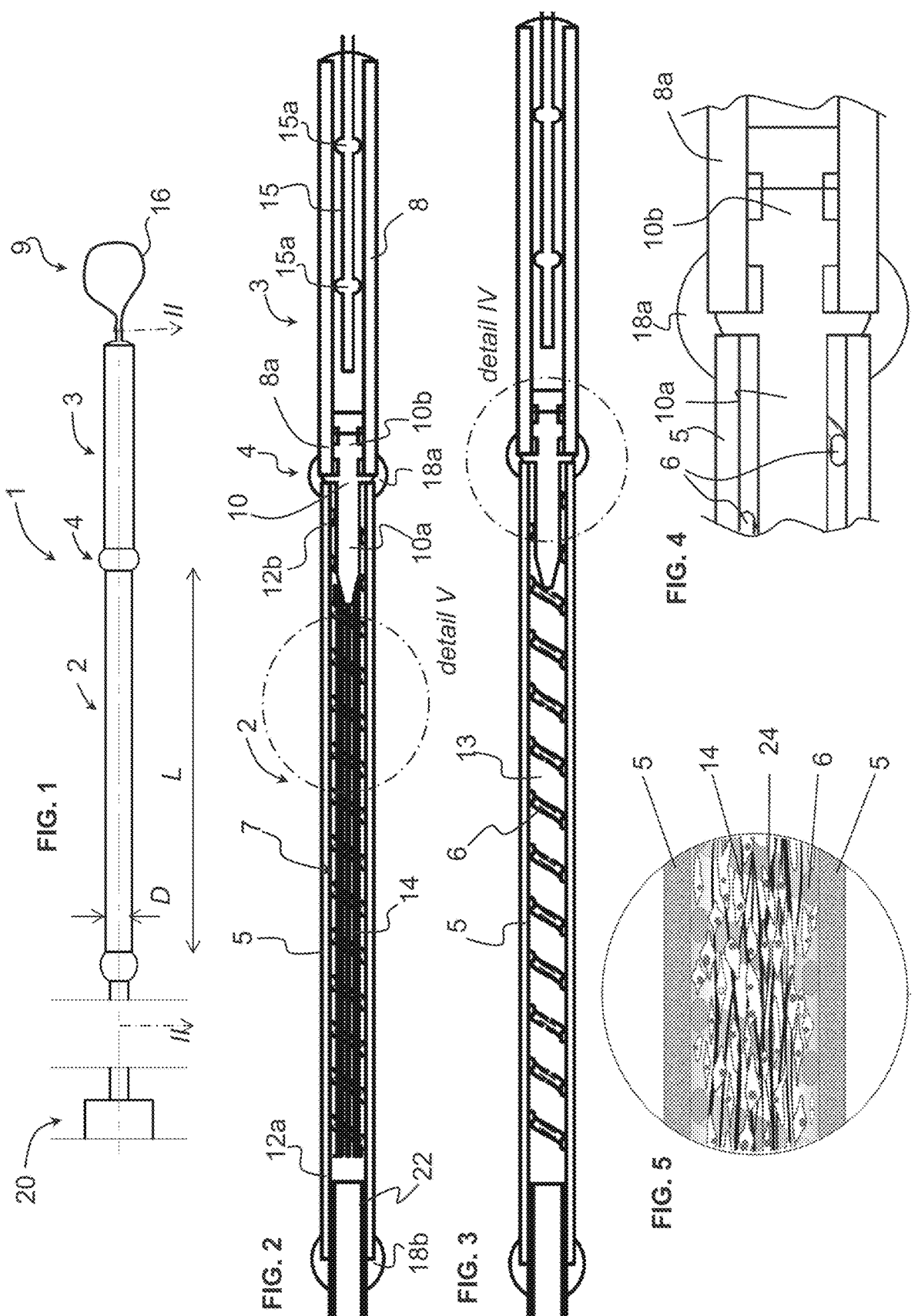

FIG. 6
A  GM-CSF delivery (in vitro)
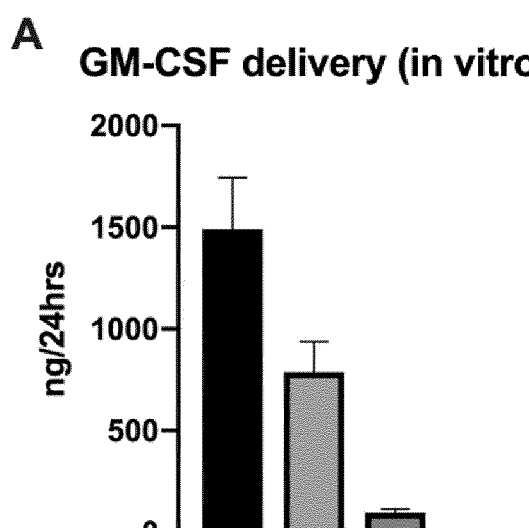
B  GM-CSF delivery after 1 week in vivo
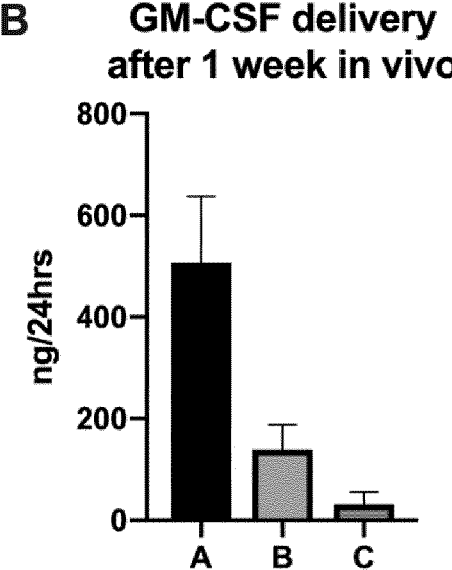
C  GM-CSF in serum after 1 week
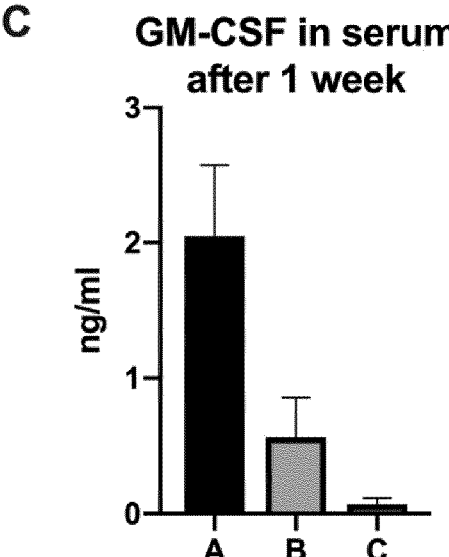
D  GM-CSF in tissue after 1 week
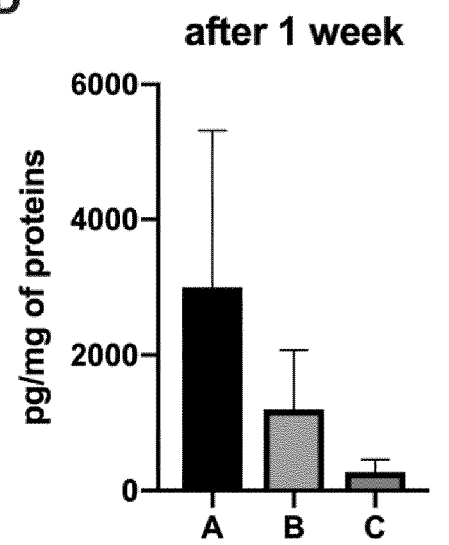

IMPLANTABLE CAPSULE

FIELD OF THE INVENTION

This invention relates to an implantable capsule for encapsulation of cells for the release of therapeutic proteins or adjuvants. The present invention may in particular be used in the field of encapsulation of immortalized cell lines for the release of therapeutic proteins or adjuvants.

BACKGROUND OF THE INVENTION

Cell encapsulation technology allows for chronic and/or localized administration of macromolecules in multiple domains. It is based on the implantation in a subject of one or several biocompatible capsules containing genetically modified cells to produce a therapeutic protein of interest. This type of capsule is generally made up of a semipermeable membrane that provides a mechanical protection to the modified cells, thus avoiding the contact between said cells and the immune cells of host and resulting in prolonged survival of the encapsulated cells. In addition, the semipermeable membrane allows the influx of nutrients and oxygen to the transplanted cells and the efflux of the protein of interest to the host, thus allowing a sustained production.

Ex vivo gene therapy using retrievable encapsulated cellular implants has been developed as an effective strategy for the local and/or chronic delivery of therapeutic proteins. In particular, modulating the activity of the immune system of a patient has been considered as an innovative approach for the treatment of various disorders and in particular, therapeutic schemes using genetically engineered encapsulated cells have been developed such as chronic administration of monoclonal antibodies for passive immunization against neurodegenerative diseases and the local delivery of a cytokine as an adjuvant for anti-cancer vaccines (Lathuilière et al., 2015, *Int. J. Mol. Sci.*, 16, 10578-10600 and Schwenter et al., 2011, *Cancer Gene Therapy.*, 18, 553-562).

It has been recently developed a technique for anti-cancer active immunization using encapsulated cells secreting granulocyte-macrophage colony stimulating-factor (GM-CSF) allowing the standardized release of GM-CSF by the genetically modified allogeneic cells (MVX-1 cells) which has immune-protective and boosting activities useful for tumor regression. Patient immunizations is performed in healthy skin, distant from tumor deposits by combining irradiated autologous tumor cells and 2 capsules containing MVX-1 cells, producing >20 ng/24 h of huGM-CSF. This permits the production of GM-CSF and exposes the immune system to the tumor-associated antigens (TAA) expressed by the autologous tumor cells at the injection site. Local expression of GM-CSF recruits and activates antigen-presenting cells (APC), which induces both antibody-dependent cell-mediated cytotoxicity (ADCC) and cytotoxic T-lymphocyte responses at the site of the injection and systemically (WO 2017/064571). Results of the clinical trial using those capsules were reported in *Annals of Oncology*, 2015, 26 (suppl_8): 1-4. 10.1093/annonc/mdv513.

In order to optimize the human application of encapsulation technologies, a critical point is the generation of an implantable, safe and effective human cell lines as a platform for the in vivo secretion of recombinant proteins of interest. Therefore, there is a need for the development of efficient cell lines particularly suitable for encapsulation technology in terms of safety and long-lasting effects. Further, for some applications, there is a need to freeze the cells for their preservation and transport, and developing capsules ensuring a high level of survival of the cells during storage and transport, in particular after thawing of the frozen cells is of high interest for promoting therapeutic strategies with encapsulated cells.

Depending on the application and treatment regimen, implanted capsules may remain in the patient's body for extended periods of time, ranging from a few days to a few months. For the comfort of the patient, and in particular to facilitate implantation and removal of the capsule with minimal discomfort, it is desirable to have a particularly compact and small diameter implant. The internal volume of the capsule and the surface area of the membrane in the contact with the surrounding tissue however influences cell survival, and consequently the amount of therapeutic proteins or adjuvants released from the capsule.

In order to have a particularly compact implantable capsule it is therefore desirable to have a system that allows efficient encapsulation of the cells with a high yield and rate of release of the desired therapeutic agents.

SUMMARY OF THE INVENTION

In view of the foregoing, an object of the invention is to provide an implantable capsule for encapsulation of cells for the release of therapeutic agents that is compact and easily implantable and removable, yet that allows for a high yield and rate of release of therapeutic agents of interest.

It is advantageous to provide an implantable capsule that is well adapted for encapsulation of both adherent and non-adherent cells.

It is advantageous to provide an implantable capsule for encapsulation of cells that preserves the activity of the cells over an extended period of time.

It is advantageous to provide an implantable capsule for encapsulation of cells that may be used in different treatments with different types of cells.

It is advantageous to provide an implantable capsule that is easy to insert and to extract with minimal discomfort to the patient.

It is useful to provide an implantable capsule which is able to be frozen and thawed, while maintaining the encapsulated cells in good surviving conditions such that their ability to secrete high levels of a protein interest is preserved after thawing.

Objects of this invention have been achieved by providing the system described herein.

Disclosed herein is an implantable capsule comprising a cell receiving portion comprising a porous membrane surrounding a cell receiving chamber for receiving immortalized cells in a liquid media therein for the secretion of therapeutic agents, characterized in that the capsule further comprises a cell support matrix inserted within the cell receiving chamber configured for the arrangement of the immortalized cells within the cell receiving chamber. The cell support matrix comprises at least one yarn.

By "yarn" it is meant, as per se commonly understood, a plurality of strands of fibres woven or spun together to form a string.

In an advantageous embodiment, said at least one yarn consists of, or comprises, a polyester material.

In an advantageous embodiment, the cell support matrix comprises a plurality of said yarns.

In an advantageous embodiment, the plurality of yarns is in a range of 5 to 20 yarns, preferably a range of 5 to 15 yarns, for instance around 10 yarns.

In an advantageous embodiment, the yarns extend within the cell receiving chamber over substantially the whole length of the chamber or at least 80 percent of the length of the cell receiving chamber.

In an advantageous embodiment, the cell receiving chamber comprises polyester yarns.

In an advantageous embodiment, the cell receiving portion further comprises a membrane support mounted in the cell receiving chamber configured for providing structural support to the porous membrane, the membrane support consisting of or comprising a coil made of a biocompatible material, for instance of stainless steel coil.

In an advantageous embodiment, the capsule further comprises an extractor portion coupled to an extractor end of the cell receiving portion configured for allowing a surgical tool to pull the implantable capsule out of an implantation site, the extractor portion comprising a retrieval thread.

In an advantageous embodiment, the retrieval thread is made of a thread of polypropylene.

In an advantageous embodiment, the extractor portion comprises an anchor tube (8) having a cavity therein within which an anchor portion (15) of a retrieval thread (9) is inserted and bonded.

In an advantageous embodiment, the anchor tube consists of or comprises a polyurethane material.

In an advantageous embodiment, the extractor portion is coupled to the cell receiving portion via a coupling comprising a connector, a connector comprising a portion inserted into an extractor end of the porous membrane and second portion inserted in a coupling end of the anchor tube.

In an advantageous embodiment, the connector is bonded to the anchor tube and the cell receiving portion by an adhesive, in particular a light curable adhesive, for instance of the type photocurable urethane methacrylate.

In an advantageous embodiment, an outer diameter of the capsule is in a range of 0.5 to 3 millimeters preferably in a range of 0.8 to 1.5 millimeters and has a length in a range of 5 to 25 millimeters preferably in a range of 8 to 20 millimeters.

In an advantageous embodiment, a length to diameter ratio of the capsule is in a range of 5 to 20.

Further objects and advantageous aspects of the invention will be apparent from the following detailed description and accompanying figures.

BRIEF DESCRIPTION OF THE DRAWINGS

The invention will now be described with reference to the accompanying drawings, which by way of example illustrate embodiments of the present invention and in which:

FIG. 1 is a schematic illustration of an implantable capsule according to an embodiment of this invention;

FIG. 2 is a cross-sectional view through line II-II of FIG. 1;

FIG. 3 is a cross-sectional view similar to FIG. 2 with an internal matrix of the capsule removed;

FIG. 4 is a detailed view of circle IV of FIG. 3;

FIG. 5 is a detailed view of circle V of FIG. 2;

FIG. 6 illustrates results of tests with a conventional capsule and a capsule according to an embodiment of the invention.

DETAILED DESCRIPTION OF EMBODIMENTS OF THE INVENTION

Referring to the figures, an implantable capsule 1 according to an embodiment of invention comprises a cell receiving portion 2 and an extractor portion 3 connected together by a coupling 4. The cell receiving portion 2 comprises a substantially cylindrical outer shape with a diameter that may typically be in the range of 0.5 to 3 millimeters and a length that may be typically in the range of 5 to 20 millimeters for instance around 10 millimeters. The ratio L/D of the length L to the diameter D is preferably in a range from 5 to 20 preferably in a range from 5 to 15. The capsule may be implanted in a patient's tissue by means of implantation devices that are per se well-known in the field of implants and need not be further described herein.

The cell receiving portion 2 comprises a porous membrane 5 that is configured for allowing therapeutic agents produced by the cells 24 contained in the capsule through the membrane to the surrounding tissue and to allow fluids and electrolytes and nutrients for the cells 24 to pass into the capsule through the membrane from the surrounding tissue.

The porosity and the type of membrane may thus depend on the specific application and type of cells that are contained within the capsule. In an example, the membrane is for instance in a form of a polyether-sulfone (PES) membrane having a porosity around 0.65 μm configured to allow the target molecules to pass though the membrane. An example of a membrane may be used in the present invention is detailed hereafter:

An exemplary embodiment of a membrane comprises polyethersulfone based on its biocompatible chemical composition, the structure properties as well as the inherent membrane performance, such as the superior flow rates, the downstream cleanliness and the low protein binding affinity. It can be extruded in different shapes and in small diameter tubing.

The cell receiving portion 2 can have the form of a flat sheet as described in Lathuillère et al., 2014, *Biomaterials* 35 780-790 or WO 2014/173441 or hollow fiber such as described in Lathuillère et al., 2015, supra, depending on the secreted protein and the site of implantation of the device.

The cell receiving portion 2 may contain an effective amount of cells such as for example between about $1.0 \times 10^4$ cells and $8 \times 10^5$ cells according to interest (e.g., $1.0 \times 10^4$, $5.0 \times 10^4$, $1.0 \times 10^5$, $3.0 \times 10^5$, $5.0 \times 10^5$ or $8 \times 10^5$ or $10^6$ cells), depending on the application and the secreted protein. Those skilled in the art will recognize that the exact cell number in the cell receiving portion can depend both upon the growth rate of the cell/cell line encapsulated and/or the volume of the cell receiving portion.

The porous membrane 5 surrounds a cell receiving chamber 13 and a membrane support 6 within the cell receiving chamber 13. The membrane support serves to mechanically support the porous membrane to maintain the stability of the volume in the cell receiving chamber 13 and to prevent rupture of the membrane. In the illustrated embodiment, the membrane support is in a form of a coil, in particular a stainless steel coil that is per se known for instance as described in WO 2017/0645701. The membrane support 6 also serves to anchor the extractor portion 3 via the coupling 4.

In the illustrated embodiment, the coupling 4 comprises a connector 10 having a portion 10a that is inserted into the membrane support 6, in particular within the cylinder surrounded by the stainless steel coil in the present example. The diameter of the connector insert portion 10a may be configured to engage in a tight fit in an extractor end of the coil for a stable connection therebetween. The coupling 4 further comprises a fixing portion 10b engaging an anchor 8 of the extractor portion 3, whereby in the presently illustrated embodiment the anchor 8 is in the form of a tube, preferably a polyurethane (PU) tube fitted over the second end 10*b* of the connector 10. An adhesive 18*a* may be deposited on the connector prior to insertion of the exactor end 12*b* of the cell receiving portion, respectively coupling end 8*a* of the anchor to 8 on the connector 10. The adhesive may advantageously be in the form of a light curable adhesive for instance of the type photocurable urethane methacrylate (such as dymax 1187 M SV).

The extractor portion 3 serves to provide a means to pull out the implant from the patient's tissue at the end of its use. In the illustrated embodiment, the extractor portion further comprises a retrieval thread 9 comprising an anchor portion 15 fixed to the anchor tube 8 and a thread portion 16 extending beyond the anchor tube configured for allowing a surgical device to catch the thread to pull out the implantable capsule. In the illustrated embodiment, the retrieval thread 9 is made of a biocompatible yarn or thread, for instance of the type Polypropylene (such as the Prolene™ suture).

In an embodiment, a length of the thread extends within the hollow anchor tube 8 and comprises knots 15*a*, the anchor portion 15 being held within the tube by an adhesive, for instance a light curable adhesive as described above, the knots increasing the strength of the attachment of the retrieval thread to the anchor tube. The retrieval thread is thus supple and very fine to reduce discomfort of the patient and allow easy removal of the implant.

It may be noted that the extractor portion 3 may have different shapes and configurations, the purpose being to allow a surgical device to grip on to the implant and to pull it out of the patient's tissue.

In a variant, the retrieval thread may be directly fixed to the connector 10, or be integrally formed with the connector 10, without the presence of the anchor tube. In such a variant the connector may for instance comprise an orifice allowing a thread to feed through the orifice and allow for pulling the implanted capsule out of the patient's tissue. The polyurethane tube, or any other material with the adequate mechanical and biological properties, advantageously provides a structure which supports the coupling of the retrieval thread. It may also be used as the support for the tweezers during manipulations, whether it is during the assembly or the implantation.

The cell receiving portion 2 further comprises a cell support matrix 7 inserted within the cell receiving chamber. In a preferred embodiment, the cell support matrix 7 comprises one or more yarns 14 of a biocompatible material, preferably a plurality of yarns extending longitudinally within the cell receiving chamber 13. The yarns extend, in a preferred embodiment, from a position at or proximate the extractor end 12*b* to a position at or proximate a cell loading end 12*a* of the membrane 5. The yarns preferably extend over the entire length or a large portion of the length of the cell receiving chamber 13. In a preferred embodiment, the yarns may advantageously be made of polyester (PE) of clinical grade that is per se well-known and already approved for surgical implantation uses. Such polyester yarns are typically used for sutures of tissue within a patient's body. An example of polyester yarns that may be used in advantageous embodiments of the invention is for instance 44/27-PET-5540-FTT-SS (Textile Development Associates, Inc). The material is 40 denier 27 filaments yarn made of textured polyester.

It has been found that the cell support matrix 7 significantly improves the performance of the immortalized cells contained in the cell receiving chamber increasing both activity in a release of therapeutic agents and durability over time, in particular for adherent cells. Such adherent cells are for instance genetically engineered cells useful in cell therapy such as for example genetically engineered immortalized human myoblasts, mouse myoblasts, human retinal pigment epithelial cells, stem cells, stem cell derived cell lines. Whereby it is being found that these cells 24 tend to align with the fibers of the yarn 14 thus improving the density and spacing of the cells optimized for release of therapeutic agents and ingestion of nutriments. The yarns also advantageously provide a large overall surface area for adherents of cells thereto.

In an exemplary embodiment, immortalized human myoblast cells secreting GM-CSF are loaded in the cell receiving portion 2 of a capsule of the invention. Those capsules are useful in a personalized anti-tumor cell immunotherapy.

The cells are loaded in the cell receiving portion in a cell growth medium suitable for the type of cells such as Ham's F12 or DMEM supplemented with growth factors or fetal bovine serum. Further, for cells that will be frozen, a freezing medium/cryopreservant is also added to the cell growth medium, such as for glycerol.

In an exemplary embodiment, a cell receiving cavity 13 may receive therein for instance five to twenty yarns 14 arranged in parallel within the cavity extending substantially the whole length of the cavity. The yarns may be inserted within the cell receiving cavity 13 by pulling one end thereof through the cavity, the coupling 4 being mounted on the extractor end 12*b* of the cell receiving portion 2 once the membrane support 6 and cell support matrix 14 have been mounted in the porous membrane 5.

It may be noted that the cell support matrix 7 may be preassembled to the membrane support 6, for instance by inserting them through the inside of the coil prior to the insertion of the preassembled coil and cell support matrix into the tubular porous membrane 5.

The cell support matrix 7, in particular in the form of yarns 14, thus has a very beneficial effect of optimizing the distribution of cells in an orderly manner within the cell receiving chamber, improving the secretion yield and rate for a given volume. Moreover, this configuration allows the length of the cell receiving portion to be easily modified by simply changing the cut length of the yarns to the corresponding length of the porous membrane tube and coil of the membrane support 6. Moreover, the use of well characterized biocompatible implantable polyester does not adversely impact the safety of the device.

It has also been observed that the presence of the cell support matrix 7 allows the freezing and thawing of cells contained without affecting the viability of the cells. The presence of the matrix 7 improves the freezing and thawing properties of the capsule which is particularly advantageous since it allows the capsules to be stored for extended periods of time in a frozen state, ready for use in the treatment of a patient when needed. In particular, it would appear that the improved distribution of cells, in particular adherent cells, along the yarns contribute to maintain a high rate of viability during the freezing and thawing process.

The cells in a liquid media may be inserted into the cell receiving chamber 13 by means of a cell loading device 20 (only partially and schematically represented in the illustrations) comprising an outlet nozzle 22 that is inserted in a cell loading end 12*a* of the porous membrane 5.

The implantable capsule 1 may be supplied in a preassembled arrangement with the cell loading device. In this embodiment, the nozzle 22 of the cell loading device may be attached to the cell loading end 12*a* of the membrane, for instance by means of an adhesive 18*c*, for instance a light curable adhesive as already described hereinabove. The cell loading device may comprise a catheter tube to allow the cells in a liquid media to be injected through the catheter tube into the cell receiving chamber of the capsule, air contained within the cell receiving capsule being pushed out through the porous membrane 5.

As noted above however, the capsule may be filled with the immortalized cells and the media in a ready to use state the cell receiving end 12 being hermetically sealed by a plug (not shown) and then frozen until needed for treatment of a patient.

According to a particular aspect, immortalized human myoblasts cells suitable in relation with the invention can be derived from primary human myoblast cells, wherein said cells express CDK4 and hTERT and retain myoblast features and further genetically engineered to secrete a protein of interest such as human, humanized or chimeric monoclonal antibodies (or recombinant proteins (e.g. mouse or human) and the like.

According to a further particular aspect, immortalized human myoblast cell line suitable in relation with the invention can be immortalized human myoblast cell line deposited with CCOS under accession number 1902 or a composition or a progeny thereof that can be further genetically engineered to secrete a protein. For example, those cells can be advantageously transduced for the expression of a target protein under the control of interest under the control of a promoter which is overactivated in hypoxia condition such as PGK (phosphoglycerate kinase) promoter, in particular human phosphoglycerate kinase (hPGK) promoter as described in Salmon, 2013, *Methods Mol Biol.;* 945:417-48.

According to a further particular aspect, immortalized human myoblasts cells suitable in relation with the invention can be derived from primary human myoblast cells, wherein said cells express CDK4 and hTERT and retain myoblast features and further genetically engineered to secrete GM-CSF. For example, immortalized human myoblast cell line suitable in relation with the invention can be genetically engineered immortalized myoblast cells for GM-CSF secretion deposited under number COOS 1901 (derived cell line deposited under number COOS 1902).

Example 1: Testing of a Capsule of the Invention for the Delivery of Human GM-CSF In Vitro and In Vivo In the following experiments, two types of implantable capsules are compared: a capsule as described in FIG. 1 for Groups A and B, vs a capsule as described in WO 2017/064571 (conventional capsule) for comparative Group C.

Group A: capsules are loaded with cells of the invention (immortalized human myoblast cell line expressing human GM-CSF (cell line deposited under number CCOS1901).

Group B: capsules are loaded with a control cell line: K562 human erythroleukemia cells expressing human GM-CSF.

Group C: capsules are loaded with the same control cell line: K562 human erythroleukemia cells expressing human GM-CSF.

The conventional capsule does not enclose any supporting matrix, therefore it is not suited to be loaded with adherent cells such as human myoblast. To compare the efficacy of the two distinct capsules to produce huGM-CSF over time we used the K562 human erythroleukemia cell line expressing human GM-CSF.

Data of Group B and C provide a direct comparison of the performance of the capsule of the invention as it is a head to head comparison of 2 distinct capsules containing the same genetically engineered cell line expressing the same therapeutic protein of interest. Data for Group A provides supports the particular advantage of the combination of a capsule of the invention with adherent cells such as immortalized human myoblast cell over: K562 human erythroleukemia cells is a standard capsule for the expression of a protein of interest as GM-CSF (Group C).

Under sterile culture condition, approximately 800,000 cells were loaded into capsules. Capsules were maintained in culture medium at 37° C. and 5% $CO2$. The delivery of human GM-CSF was quantified in culture medium using an ELISA (Kit #KHC2011, Thermo Fischer) and reported in ng/24 hrs (FIG. 6A).

Capsules were implanted in the mouse subcutaneous tissue for 1 week. After sacrifice, the capsules were retrieved from animals and placed in culture medium for the quantification of human GM-CSF delivery (FIG. 6B). In addition, GM-CSF was quantified in the mouse serum (FIG. 6C) as well as in the subcutaneous tissue surrounding the capsules (FIG. 6D).

Those data support that the capsule of the invention is particularly useful for the culture of adherent cells such as immortalized human myoblast cells since it allows achieving a sustained, stable GM-CSF and most efficient production both in-vitro and in-vivo by encapsulated cells.

LIST OF REFERENCES IN THE DRAWINGS

Capsule 1
    Cell receiving portion 2
        Cell Loading end 12*a*
        Extractor end 12*b*
        Porous Membrane 5
            PES membrane
            cell receiving chamber 13
        Membrane Support 6
            coil
                stainless steel coil
        Cell support matrix 7
            yarn(s) 14
                polyester yarns
    Extractor portion 3
        Anchor 8
            Tube
            coupling end 8*a*
        retrieval thread 9
            anchor portion 15
                anchor knot 15*a*
            thread portion 16
            adhesive 18*a*
        Coupling 4
            connector 10
            adhesive 18*b*
                (light) curable adhesive
    Cell loading device 20
        Outlet nozzle 22
        Coupling (cell loading device to capsule)
            adhesive 18*c*
    Cells 24
    Membrane diameter D (external)
    Membrane length L
    Ratio of length/diameter L/D

The invention claimed is:

1. An implantable capsule comprising a cell receiving portion comprising:

(a) a porous membrane surrounding a cell receiving chamber for receiving genetically engineered immortalized cells in a liquid media therein for the secretion of therapeutic agents, and (b) a membrane support mounted in the cell receiving chamber configured for providing structural support to the porous membrane, the membrane support comprising a coil made of a biocompatible material, wherein the capsule further comprises a cell support matrix comprising at least one yarn inserted within the cell receiving chamber configured for the arrangement of the immortalized cells within the cell receiving chamber, said coil surrounding said at least one yarn.

2. The implantable capsule according to claim 1, wherein said at least one yarn comprises a polyester material.

3. The implantable capsule according to claim 1, wherein the cell support matrix comprises a plurality of said yarns.

4. The implantable capsule according to claim 3, wherein the plurality of yarns is in a range of 5 to 20 yarns.

5. The implantable capsule according to claim 3, wherein the plurality of yarns is in a range of 5 to 15 yarns.

6. The implantable capsule according claim 1, wherein the at least one yarn extends within the cell receiving chamber over at least 80% of a length of the cell receiving chamber.

7. The implantable capsule according to claim 1 further comprising an extractor portion coupled to an extractor end of the cell receiving portion configured for allowing a surgical tool to pull the implantable capsule out of an implantation site, the extractor portion comprising a retrieval thread.

8. The implantable capsule according to claim 7, wherein the retrieval thread is made of a thread of polypropylene.

9. The implantable capsule according to claim 7, wherein the extractor portion comprises an anchor tube having a cavity therein within which an anchor portion of a retrieval thread is inserted and bonded.

10. The implantable capsule according to claim 9, wherein the anchor tube consists of or comprises a polyurethane material.

11. The implantable capsule according to claim 9, wherein the extractor portion is coupled to the cell receiving portion via a coupling comprising a connector, a connector comprising a portion inserted into an extractor end of the porous membrane and second portion inserted in a coupling end of the anchor tube.

12. The implantable capsule according to claim 11, wherein the connector is bonded to the anchor tube and the cell receiving portion by an adhesive.

13. The implantable capsule according to claim 12, wherein the adhesive is a light curable adhesive.

14. The implantable capsule according to claim 1, wherein an outer diameter of the capsule is in a range of 0.5 to 3 millimeters and has a length in a range of 5 to 25 millimeters.

15. The implantable capsule according to claim 1, wherein a length to diameter ratio of the capsule is in a range of 5 to 20.

16. The implantable capsule according to claim 14, wherein the capsule has an outer diameter in a range of 0.8 to 1.5 millimeters.

17. The implantable capsule according to claim 14, wherein the capsule has a length in a range of 8 to 20 millimeters.

* * * * *